United States Patent [19]
Balogh et al.

[11] Patent Number: 4,980,346
[45] Date of Patent: Dec. 25, 1990

[54] SYNERGISTIC FUNGICIDAL AND ACARICIDAL AND COMPOSITIONS CONTAINING TWO OR THREE ACTIVE INGREDIENTS

[75] Inventors: Károly Balogh, Miskolc; Márta Bartha née Kocsis, Sajóbábony; Zsuzsa Dancs née Rozsnyai, Budapest; Erzsébet Grega née Tóth, Miskolc; Magdolna Magyar née Tömörkényi, Miskolc; István Nagy, Miskolc; József Nagy, Miskolc; Gyöngyvér S. Nagy née Hegyi, Budapest; Gyula Oros, Budapest; Csaba Pavliscsák, Sajóbábony; Károly Pásztor, Miskolc; Gyula Tarpai, Miskolc; Eszter Urszin née Simon, Sajóbábony, all of Hungary

[73] Assignee: Eszakmagyarorsuagi Vegyimuvek, Sajobabony, Hungary

[21] Appl. No.: 296,451

[22] Filed: Jan. 11, 1989

[30] Foreign Application Priority Data

Jan. 14, 1988 [HU] Hungary .................................. 129/88
Oct. 27, 1988 [HU] Hungary .................................. 129/88

[51] Int. Cl.$^5$ ..................... A01N 43/52; A01N 43/60; A01N 57/00

[52] U.S. Cl. ..................................... 514/118; 514/255; 514/388

[58] Field of Search ......................... 514/118, 255, 388

[56] References Cited

U.S. PATENT DOCUMENTS 3,657,443  4/1972  Klopping ............................. 424/273

OTHER PUBLICATIONS

Worthing et al.; The Pesticide Manual, 9th Ed. (1987) pp. 127, 128, 834 and 835.
Eszakmagyarorszagi; C. A., vol. 105, (1986) 105:191613w.

*Primary Examiner*—Allen J. Robinson
*Attorney, Agent, or Firm*—Herbert Dubno; Jonathan Myers

[57] ABSTRACT

The invention relates to synergistic fungicidal and acaricidal compositions containing two or three active ingredients in a ratio of 10:1–1:10 and 20:1:1–1:10:10, selected from the group of N-alkyl(ene)-N-(0,0-disubstituted-thiophosphoryl)-N', N'-substituted glycine amide derivatives, Triforine, Carbendazim, copper-oxyquinolate, cycloheximide, Mancozeb, benzimidazole derivatives, phenyl amide derivatives F-849, Folpet, Captofol, Iprodione or S-39475.

3 Claims, No Drawings

SYNERGISTIC FUNGICIDAL AND ACARICIDAL AND COMPOSITIONS CONTAINING TWO OR THREE ACTIVE INGREDIENTS

FIELD OF THE INVENTION

The invention relates to synergistic fungicidal and acaricidal compositions containing two or three active ingredients.

The compositions according to the invention contain in a total amount of 0.001–95% by weight and in a ratio of 10:1–1:10 and 20:1:1–1:10:10 respectively, a N-alkyl-(ene)-N-(0,0-disubstituted-thiophosphoryl)-N'-N'-disubstituted glycine-amide of the formula (I)

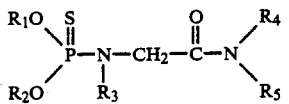

and Triforine (N,N'-bis (1-formamido-2,2,2-trichloroethyl)-piperazine) and/or copper-oxy-quinolate or cycloheximide (4-(2R)-2-[(1S,3S,5S)-(3,5-dimethyl-2-oxo-cyclohexyl)]-2-hydroxyethyl)-piperidin-2,6-dione) or Mancozeb ([Mn+Zn] ethylene-bis-dithiocarbamate) and/or a benzimidazole derivative of the formula (II)

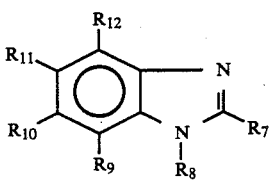

and/or a phenylamide derivative of the formula (III)

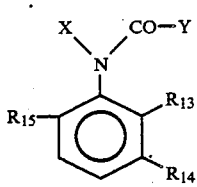

and/or F-849 of the formula (IV)

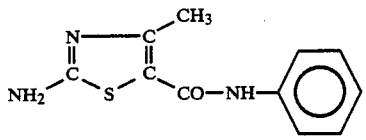

and/or Folpet (N-(trichloro-methylthio)-phthalimide) and/or Captafol (N-(1,1,2,2-tetrachloro-ethylthio)-tetrahydro-phtalimide) and/or Iprodione (1-isopropyl-carbamoyl-3-(3,5-dichlorophenyl)-hydantoine) and/or Nystatin and/or Quintozene (pentachloro-nitrobenzene), and/or S-39475 (3,4-diethoxyphenyl-isopropyl-carbamate) as active ingredient in admixture with known solid or liquid carriers or diluents and other additives, e.g. emulsifying, dispersing, wetting, stabilizing agents and activity enhancer.

Background of the Invention

The N-alkyl(ene)-N-(0,0-disubstituted thio-phosphoryl)-N,N'-disubstituted glycine amides of the formula (I) are described in Hungarian patent No. 194258 and can be used widely in case of various fruits (e.g. apple, pear, apricot, peach, plum, grape), vegetables (e.g. bean, soybean), cultures (e.g. hop) and ornamental plants (e.g. rose, gerbera, pink) against different pests, such as phytophage mites, various insects, e.g. plant lice, green flies, flies, moths, as well as against certain pathogenic fungi, e.g. Phytophtora infestans, Botrytis cynerea, Podosphera leucotricha, Uromyces appendiculatus, Erwinia caraptuvora, Erysiphe graminis, Khuseia oryzae, Helminthosporium carbonum.

The fungicidal composition (Saprol) containing Triforine as active ingredient is used in orchards (e.g. apple), in grape, winter wheat and in hop cultures against powdery mildew, in stone-fruits against monilia infections and shoot-diseases, in ornamental plants, e.g. in pinks, against pink rust.

The protective fungicidal activity of the copper complex of (8-oxyquinoline) has been first described by Powell (Phytopathology, 36, p. 573, (1946)).

The fungicidal compositions containing cycloheximide as active ingredient are suggested for use against pathogenic fungi of plants.

The fungicidal composition containing Mankozeb as active ingredient (Dithane M-45) is useful for combating different diseases caused by fungi, except powdery mildew. It can be used for spraying against apple scab, pear scab, brown rot of apricot, peach and cherry, red fire disease, downy mildew of grape and pink rust and for seed dressing of spring and winter cereals and sunflower, against smut fungi, generally combined with Chinoin Fundazol.

The fungicidal compositions containing benzimidazole derivatives of the formula (II) are used in agriculture and horticulture. E.g. the Kolfugo 250 FW composition containing Carbendazim (benzimidazole-2-yl-carbamic acid-methyl ester) as active ingredient (the fungicidal activity of which is disclosed in U.S. Pat. No. 3,647,443) is used in autumn and spring cereals against powdery mildew of cereals and fusarium rot of cereals, in sugar beet against cercospora leaf spot and against different plate-diseases of sunflower. Further, e.g. the Tecto 450 FW composition containing Thiabendazole (2-(thiazol-4-yl)-benzimidazole) as active ingredient is used against different storage diseases of potato and against various fungi infecting the root through the soil, e.g. against Fusarium and Rhizoctonia species.

The phenylamide derivatives of the formula (III), which may be acylalanine derivatives, e.g. Metalaxyl (methyl-N-(2-methoxy-acetyl)-N-(2,6-xylyl)-D,L-alaninate), Benalaxyl (methyl-N-phenylacetyl-N-(2,6-xylyl)-D,L-alaninate) or Furalaxyl (methyl-N-(2-furoyl)-N-(2,6-xylyl)-D,L-alaninate); acetamide derivatives, e.g. Ofurace (2-chloro-N-(2,6-dimethylphenyl)-N-(tetrahydro-2-oxo-3-furanyl)-acetamide) or Oxadixyl (N-(2,6-dimethylphenyl)-2-methoxy-N-(2-oxo-3-oxazolidinyl)-acetamide), carboxamide derivatives, e.g. Cyprofuram (N-(3-Chlorophenyl)-N-(tetrahydro-2-oxo-3-furanyl)-cyclopropane carboxamide) are the active ingredients of systemic fungicides, e.g. Ridomil, Galben, Fongarid, Caltan, Sandofan Vinicur which are useful against Oomycetes fungi, especially in agriculture and horticulture. These active ingredients, compositions and their application are described e.g. in the Pesticide Manual, 1983. The fungicidal compositions (e.g. Buvicid, Folpan, Ortho-Phaltan, Difolatan) containing phthalimide derivatives, e.g. Folpet or Captafol can be used for protecting grape and various fruits and vegetables against fungal attack, except powdery mildew.

The fungicidal compositions (e.g. Rovral, Botrilex) containing Iprodione or Quintozene as active ingredient are used against fungal diseases of cereals, vegetables and ornamental plants, e.g. against Botrytis, Sclerotium and Rhizoctonia species.

DESCRIPTION OF THE INVENTION

The F-849 and S-39475 are new compounds having fungicidal activity, and the activity spectrum of which is now under examination.

We have found that when admixing compounds of the formula (I) having acaricidal activity with one or two other compounds having fungicidal activity, selected from Triforine, copper-oxy-quinolate, cycloheximide, Mankozeb, benzimidazole derivatives of the formula (II), phenylamide derivatives of the formula (III), F-849 of the formula (IV), Folpet, Captofol, Iprodione, Nystatine, Quintozene or S-39475, synergistic fungicidal and acaricidal compositions can be obtained.

The present invention therefor provides synergistic fungicidal and acaricidal compositions containing two or three active ingredients in a total amount of 0.001–95% by weight and in a ratio of 10:1–1:10 and 20:1:1–1:10:10, selected from the group of N-alkyl(ene)-N-(0,0N'-disubstituted-glycine-amide of the formula (I) - wherein $R_1$ and $R_2$ are the same and stand for alkyl having 1–4 carbon atoms optionally substituted by one or two halogen atoms or alkoxy having 1–3 carbon atoms, cycloalkyl having 3–6 carbon atoms, alkenyl having 2–6 carbon atoms or phenyl optionally substituted by halogen atom, $R_3$ stands for alkyl having 1–6 carbon atoms, alkenyl having 2–6 carbon atoms or alkoxy-alkyl wherein both alkyl moieties contain 1–3 carbon atoms, $R_4$ and $R_5$ are the same and stand for alkyl having 1–4 carbon atoms, alkenyl having 2–6 carbon atoms, or $R_4$ and $R_5$ are different and stand for hydrogen, alkyl having 1–6 carbon atoms, alkenyl having 2–6 carbon atoms, cycloalkyl having 3–6 carbon atoms, phenyl, benzyl, phenyl substituted by one or two alkyl groups having 1–3 carbon atoms or halogen atoms and/or trihalogenmethyl, alkoxy-alkyl wherein both moieties contain 1–3 carbon atoms, a group of formula—$(CH_2)_n$—$R_6$, wherein n is 0–3, and $R_6$ stands for 1,2,4-triazolyl, 3-furyl, 2-furyl, 2-thienyl, pyrrolidinyl, pyranyl, pyridyl, 2-imidazolyl, 2-imidazolin-4-yl, oxazolyl, thiadiazolyl, piperidyl, morpholinyl, aziridinyl, thiolanyl, 1,3-dioxolanyl or $R_4$ and $R_5$ together with the adjacent nitrogen atom form a hexamethylene imino group and Triforine and/or copper-oxy-quinolate or cycloheximide or Mankozeb and/or benzimidazole derivative of the formula (II) - wherein $R_7$ stands for alkyl having 1–6 carbon atoms optionally substituted by one or more halogen atoms, amino optionally substituted by methoxycarbonyl, cyano, group of formula CS—NH—R' wherein R' stands for hydrogen atom, alkyl having 1–4 carbon atoms, alkenyl having 2–4 carbon atoms, alkynyl, alkoxycarbonyl, cycloalkyl, aryl or acyl, further $R_7$ may also be a 4–6 membered heterocyclic group comprising 1–3 hetero atoms selected from the group of oxygen and/or sulphur and/or nitrogen, $R_8$ stands for hydrogen, —CO—NH—$C_4H_9$, —CO—NH—$(CH_2)_5$—CN, benzoyloxy or a group of formula $SO_2$—R" wherein R" is alkyl having 1–4 carbon atoms substituted by one or more halogen atoms; cycloalkyl, amino optionally substituted by one or two alkyl; groups or a 4–6 membered heterocyclic group containing 1–3 heteroatoms selected from the group of oxygen and/or sulphur and/or nitrogen, $R_9$, $R_{10}$, $R_{11}$ and $R_{12}$ independently from each other stand for a hydrogen atom, a halogen atom, alkyl having 1–4 carbon atoms, alkenyl having 2–4 carbon atoms, alkynyl having 2–4 carbon atoms, each optionally substituted by one or more halogen atoms, alkoxy, alkenyloxy, alkynyloxy, alkylthio, alkenylthio, alkynylthio, alkoxycarbonyl or acyl, each containing a maximum of 6 carbon atoms, aryl, nitro, cyano, isocyanato, thiocyanato, iso-thiocyanato, amino, sulfamoyl, aryloxy, alkyl-$SO_n$, aryl-$SO_n$- wherein n is 0–2 and/or phenylamide derivative of the formula (III) wherein x stands for a hydrogen atom, alkoxycarbonyl-alkyl, wherein both alkyl moieties contain 1–3 carbon atoms, tetrahydro-2-oxo-3-furanyl, 2-oxo-3-oxazolidinyl, 3-methyl-4,5-isoxazol-dione-imino, y stands for a hydrogen atom, alkyl having 1–4 carbon atoms optionally substituted by 1–3 halogen atoms, cycloalkyl having 3–6 carbon atoms, alkoxy-alkyl, wherein both alkyl moieties contain 1–3 carbon atoms, phenyl, benzyl or 4–6 membered heterocyclic groups comprising 1–3 heteroatoms selected from the group of oxygen and/or sulphur and/or nitrogen, $R_{13}$, $R_{14}$ and $R_{15}$ stand independently from each other, for a hydrogen atom, a halogen atom, alkyl having 1–3 carbon atoms, alkenyl or alkynyl both having 2–4 carbon atoms and/or F-849 of the formula (IV) and/or Folpet and/or Captofol and/or Iprodione and/or Nystatin and/or Quintozene and/or S-39475, in admixture with known solid or liquid carriers and/or diluents and optionally other additives, e.g. emulsifying, dispersing, wetting, stabilizing agents and activity enhancers.

A carrier in a composition according to the invention is any material with which the active ingredient is formulated to facilitate application to the locus to be treated, which may for example be a plant, seed or soil, or to facilitate storage, transport or handling. A carrier may be a solid or a liquid including a material which is normally gaseous but which has been compressed to form a liquid and any of the carriers normally used in formulating pesticidal and fungicidal compositions may be used.

Suitable solid carriers include e.g. synthetic silicates, diatomaceous earth, talc.

Suitable liquid carriers include e.g. optionally halogenated hydrocarbons, aromatic hydrocarbons, dimethyl formamide.

Agricultural compositions are often formulated and transported in a concentrated form which is subsequently diluted by the user before application. The presence of small amount of a carrier which is a surface-active agent facilitates this process.

A surface-active agent may be an emulsifying agent, a dispersing agent or a wetting agent; it may be nonionic or ionic.

The compositions of the invention may for example be formulated as wettable powders, dusts, granules, solutions, emulsifiable concentrates, emulsions, suspensions, suspension concentrates. The emulsifiable concentrates, wettable powders and dusts are preferred.

The invention further provides a method of controlling pests and fungi, which comprises applying a composition according to the invention in a sufficient amount to the plant.

The preferred compounds of formula (I) used as one of the active ingredients in the compositions according to the invention are summarized in the following Table I.

TABLE I

| No. | $R_1$ | $R_2$ | $R_3$ | $R_4$ | $R_5$ |
|---|---|---|---|---|---|
| 1. | ethyl | ethyl | ethyl | phenyl | methyl |
| 2. | ethyl | ethyl | ethyl | phenyl | ethyl |
| 3. | ethyl | ethyl | ethyl | phenyl | i-propyl |
| 4. | ethyl | ethyl | allyl | allyl | H |
| 5. | ethyl | ethyl | allyl | i-propyl | phenyl |
| 6. | ethyl | ethyl | i-propyl | phenyl | i-propyl |
| 7. | chloro-ethyl | chloro-ethyl | allyl | allyl | H |
| 8. | ethyl | ethyl | ethyl | 2,6-di-ethyl-phenyl | H |
| 9. | ethyl | ethyl | ethyl | 2,6-di-methyl-phenyl | H |
| 10. | ethyl | ethyl | ethyl | 2-methyl-6-ethyl-phenyl | H |
| 11. | ethyl | ethyl | ethyl | allyl | allyl |
| 12. | ethyl | ethyl | methyl | n-propyl | n-propyl |
| 13. | ethyl | ethyl | n-propyl | n-propyl | n-propyl |
| 14. | ethyl | ethyl | i-propyl | n-propyl | n-propyl |
| 15. | ethyl | ethyl | n-butyl | n-propyl | n-propyl |
| 16. | ethyl | ethyl | i-butyl | n-propyl | n-propyl |
| 17. | ethyl | ethyl | ethyl | n-propyl | n-propyl |
| 18. | ethyl | ethyl | ethyl | ethyl | ethyl |
| 19. | ethyl | ethyl | allyl | ethyl | ethyl |
| 20. | ethyl | ethyl | i-propyl | ethyl | ethyl |
| 21. | ethyl | ethyl | allyl | n-propyl | n-propyl |
| 22. | ethyl | ethyl | ethyl | cyclo-hexyl | H |
| 23. | ethyl | ethyl | ethyl | hexa-methylene | |
| 24. | ethyl | ethyl | ethyl | 3-chlor-phenyl | H |
| 25. | n-butyl | n-butyl | ethyl | allyl | allyl |
| 26. | i-butyl | i-butyl | allyl | allyl | allyl |
| 27. | n-propyl | n-propyl | ethyl | allyl | allyl |
| 28. | ethyl | ethyl | ethyl | 3,4-di-chlor-phenyl | H |
| 29. | ethyl | ethyl | ethyl | cyclo-hexyl | methyl |
| 30. | methyl | methyl | ethyl | benzyl | H |
| 31. | ethyl | ethyl | ethyl | n-butyl | n-butyl |
| 32. | ethyl | ethyl | ethyl | 4-tri-fluoro-methyl-phenyl | n-butyl |
| 33. | ethyl | ethyl | ethyl | 4-bromo-phenyl | H |
| 34. | methyl | methyl | ethyl | 4-fluoro-phenyl | H |
| 35. | ethyl | ethyl | ethyl | 4-methyl-phenyl | H |
| 36. | allyl | allyl | ethyl | allyl | allyl |
| 37. | phenyl | phenyl | ethyl | n-propyl | n-propyl |
| 38. | cyclo-hexyl | cyclo-hexyl | ethyl | allyl | allyl |
| 39. | methoxy-ethyl | methoxy-ethyl | ethyl | allyl | allyl |
| 40. | ethoxy-ethyl | ethoxy-ethyl | ethyl | n-propyl | n-propyl |
| 41. | ethyl | ethyl | ethyl | 2,6-diethyl-phenyl | ethoxy-methyl |
| 42. | ethyl | ethyl | ethyl | 2,6-diethyl-phenyl | methoxy-methyl |
| 43. | ethyl | ethyl | ethyl | 2-methyl-2-ethyl-phenyl | methoxy-methyl |
| 44. | ethyl | ethyl | ethyl | i-propyl | i-propyl |
| 45. | ethyl | ethyl | n-propyl | i-propyl | i-propyl |
| 46. | i-propyl | i-propyl | allyl | allyl | H |
| 47. | ethyl | ethyl | n-propyl | i-butyl | i-butyl |
| 48. | ethyl | ethyl | ethyl | i-butyl | i-butyl |
| 49. | ethyl | ethyl | ethyl | ethyl | cyclo-hexyl |

TABLE I-continued

| No. | R₁ | R₂ | R₃ | R₄ | R₅ |
|---|---|---|---|---|---|
| 50. | ethyl | ethyl | n-propyl | ethyl | cyclohexyl |
| 51. | ethyl | ethyl | ethyl | morpholinyl | H |
| 52. | ethyl | ethyl | n-propyl | morpholinyl | H |
| 53. | ethyl | ethyl | ethyl | piperidyl | H |
| 54. | ethyl | ethyl | n-propyl | piperidyl | H |
| 55. | methyl | methyl | ethyl | cyclohexyl | ethyl |
| 56. | methyl | methyl | n-propyl | cyclohexyl | H |
| 57. | methyl | methyl | n-propyl | phenyl | i-propyl |
| 58. | methyl | methyl | ethyl | phenyl | i-propyl |
| 59. | methyl | methyl | allyl | phenyl | i-propyl |
| 60. | methyl | methyl | n-propyl | n-propyl | n-propyl |
| 61. | methyl | methyl | n-butyl | n-propyl | n-propyl |
| 62. | methyl | methyl | i-butyl | n-propyl | n-propyl |
| 63. | methyl | methyl | allyl | n-propyl | n-propyl |
| 64. | methyl | methyl | ethyl | i-butyl | i-butyl |
| 65. | methyl | methyl | n-propyl | i-butyl | i-butyl |
| 66. | methyl | methyl | ethyl | n-propyl | n-propyl |
| 67. | ethyl | ethyl | ethyl | 2-chlorophenyl | H |
| 68. | ethyl | ethyl | ethyl | 3-trifluoromethyl-4-chlorphenyl | H |
| 69. | ethyl | ethyl | ethyl | 4-trifluoromethyl-phenyl | H |
| 70. | ethyl | ethyl | ethyl | 4-chlorphenyl | H |
| 71. | ethyl | ethyl | ethyl | 4-fluoro-phenyl | H |
| 72. | ethyl | ethyl | allyl | benzyl | H |
| 73. | ethyl | ethyl | n-propyl | benzyl | H |
| 74. | ethyl | ethyl | n-butyl | benzyl | H |
| 75. | methyl | methyl | ethyl | i-propyl | i-propyl |
| 76. | methyl | methyl | n-propyl | benzyl | H |
| 77. | ethyl | ethyl | n-propyl | i-propyl | phenyl |
| 78. | ethyl | ethyl | ethoxypropyl | n-propyl | n-propyl |
| 79. | ethyl | ethyl | ethoxypropyl | phenyl | i-propyl |
| 80. | ethyl | ethyl | ethyl | ethoxypropyl | H |
| 81. | ethyl | ethyl | n-propyl | ethoxypropyl | H |
| 82. | ethyl | ethyl | allyl | ethoxypropyl | H |
| 83. | methyl | methyl | ethyl | phenyl | i-propyl |
| 84. | chloroethyl | chloroethyl | ethyl | phenyl | i-propyl |
| 85. | phenyl | phenyl | ethyl | phenyl | i-propyl |
| 86. | 3-chlorophenyl | 3-chlorophenyl | ethyl | phenyl | i-propyl |
| 87. | chlorethyl | chlorethyl | ethyl | n-propyl | n-propyl |
| 88. | methyl | methyl | allyl | allyl | H |
| 89. | i-propyl | i-propyl | ethyl | n-propyl | n-propyl |
| 90. | ethyl | ethyl | ethyl | 2,6-dimethyl-phenyl | 1,2,4-triazolyl-1-methyl |
| 91. | cyclopropyl | cyclopropyl | methyl | cyclopropyl | 3-furyl |
| 92. | dichloromethyl | dichloromethyl | ethyl | H | 2-furfuryl |
| 93. | n-propyl | n-propyl | methyl | benzyl | 2-thienyl |
| 94. | bromoethyl | bromoethyl | allyl | allyl | 2-thenyl |
| 95. | allyl | allyl | n-hexyl | methyl | pyrrolidinyl |
| 96. | vinyl | vinyl | allyl | allyl | pyranyl |
| 97. | methoxymethyl | methoxymethyl | methyl | benzyl | pyridyl |
| 98. | methyl | methyl | n-pentyl | methyl | 2-imidazolyl |
| 99. | allyl | allyl | ethyl | ethyl | 2-imidazoline-4-yl |
| 100. | phenyl | phenyl | methyl | methyl | oxazolyl |
| 101. | ethyl | ethyl | vinyl | H | thiadiazolyl |
| 102. | methyl | methyl | n-pentyl | benzyl | piperidyl |
| 103. | ethoxymethyl | ethoxymethyl | methyl | ethyl | morpholinyl |
| 104. | cyclohexyl | cyclohexyl | methyl | n-butyl | aziridinyl |
| 105. | ethyl | ethyl | n-pentyl | n-pentyl | thiolanyl |

TABLE I-continued

| No. | R₁ | R₂ | R₃ | R₄ | R₅ |
|---|---|---|---|---|---|
| 106. | n-pentenyl | n-pentenyl | ethyl | ethyl | 1,3–dioxolanyl |

The synergistic fungicidal and acaricidal compositions according to the invention are illustrated by the following non-limiting Examples. In the Example—unless otherwise stated—the amounts of the components are always given in % by weight.

EXAMPLE 1

Emulsifiable concentrate (35 EC)

30% compound 17 of Table I (hereinafter compound I/17) and 5% of Carbendazim are dissolved in a solvent mixture comprising 28.5% of xylene and 28.5% of dimethyl formamide. To the solution thus obtained 6% of Emulsogen IP-400 (alkylphenol polyglycolether) and 2% of Emulsogen EL-400 (polyethylene glycol oleate) are added as emulsifying agents and the solution is stirred until it becomes clear, thereafter filtered. The emulsifiable concentrate thus obtained contains compound I/17 and Carbendazim in a total amount of 35% and in a ratio of 6:1.

Following the above procedure but using any other compound of Table I together with Carbendazim, similar 35 EC compositions may be prepared.

EXAMPLE 2

Wettable powder (35 WP)

In a laboratory blender 30% of compound I/17 is sprayed under stirring onto 40% of Sipernat 50 (synthetic silicate carrier) in form a melt, thereafter 5% of Carbendazim active ingredient, 15% of siliceous earth as carrier, 2% of Netzer 1S (sodium salt of aliphatic sulphonic acid) as wetting agent, 3% of Dispergiermittel 1494 (cresol/formaldehyde condensate) and 5% of sulfite waste liquor-powder as dispersing agents are added. Thereafter the mixture obtained is homogenized under stirring and finely ground in a laboratory biting cross mill, type Alpine 63C. The wettable powder composition thus obtained contains compound I/17 and Carbendazim in a total amount of 35% and in a ratio of 6:1.

Following the above procedure but using any other compound of Table I and Carbendazim, similarly 35 WP compositions may be prepared.

EXAMPLE 3

Wettable powder (35 WP)

The procedure of Example 2 is followed but instead of Carbendazim as active ingredient Triforine is used. The wettable powder composition thus obtained contains one compound of Table I and Triforine in a total amount of 35% and in a ratio of 6:1.

EXAMPLE 4

Emulsifiable concentrate (20 EC)

18% of compound I/17 and 2% of Triforine active ingredients are dissolved under stirring in a solvent mixture of 42% of xylene and 30% of N-methyl-pyrrolidone and thereafter 6.5% of Emulsogen IP-400 and 1.5% of Emulsogen EL-40 emulsifying agents are added and further the procedure of Example 1 is followed. The emulsifiable concentrate thus obtained contains compound I/17 and Triforine in an amount of 20% and in a ratio of 9:1.

EXAMPLE 5

Wettable powder (40 WP)

In a laboratory blender 35% of compound I/17 is sprayed under stirring onto 40% of Sipernat 50 carrier in form of a melt, thereafter 5% Triforine active ingredient, 10% of siliceous earth as carrier, 2% of Netzer IS as wetting agent, 3% of Dispergiermittel 1494 and 5% of sulfite waste liquor powder as dispersing agents are added and further the procedure of Example 2 is followed. The wettable powder composition thus obtained contains the compound I/17 and Triforine in a total amount of 40% and in a ratio of 7:1.

EXAMPLE 6

Emulsifiable concentrate (20 EC)

The procedure of Example 4 is followed but using 15% of compound I/17 and 5% of Triforine. The emulsifiable concentrate thus obtained contains the two active ingredients in a total amount of 20% and in a ratio of 3:1.

EXAMPLE 7

Emulsifiable concentrate (50 EC)

45% of compound I/17 and 5% of Carbendazim are dissolved in the mixture of 25% of xylene and 17% of dimethyl formamide and 6% of Emulsogen IP-400 and 2% of Emulsogen EL-400 as emulsifying agents are added under stirring and further the procedure of Example 1 is followed. The emulsifiable concentrate thus obtained contains the said two active ingredients in an amount of 50% and in a ratio of 9:1.

Following the above procedure but using any other compound of Table I and Carbendazim as active ingredients, similarly 50 EC may be obtained.

EXAMPLE 8

Emulsifiable concentrate (25 EC)

20% of compound I/17 and 5% Triforine are dissolved in the mixture of 37% of xylene and 30% of N-methyl-pyrrolidone and 5% of Emulsogen IP-400 and 3% of Emulsogen EL-400 are added under stirring and further the procedure of Example 1 is followed. The emulsifiable concentrate thus obtained contains the said two active ingredients in a total amount of 25% and in a ratio of 4:1.

EXAMPLE 9

Wettable powder (25 WP)

In a laboratory blender 15% of compound I/17 is sprayed onto 50% Sipernat 50 carrier, thereafter 10% of Triforine as active ingredient, 15% of siliceous earth as carrier, 2% of Netzer IS as wetting agent, 4% of Dispergiermittel 1494 and 4% of sulfite waste liquor powder as dispersing agents are added under stirring and further the procedure of Example 2 is followed. The wettable powder thus obtained contains the compound I/17 and Triforine in a total amount of 25% and in a ratio of 3:2.

EXAMPLE 10

Wettable powder (25 WP)

The procedure of Example 9 is followed using both active ingredients in an amount of 12.5%. The wettable powder thus obtained contains compound I/17 and Triforine in a total amount of 25% and in a ratio of 1:1.

EXAMPLE 11

Wettable powder (50 WP)

In a laboratory blender 20% of compound I/17 is sprayed onto 30% of Sipernat 50 carrier and 30% Triforine active ingredient, 10% of siliceous earth as carrier, 2% of Netzer IS as wetting agent, 2% Dispergiermittel 1494 and 6% of sulfite waste liquor powder as dispersing agents are added under stirring and further the procedure of Example 2 is followed. The wettable powder thus obtained contains the said two active ingredients in a total amount of 50% and in a ratio of 2:3.

EXAMPLE 12

Wettable powder (50 WP)

The procedure of Example 11 is followed using 15% of compound I/17 and 35% of Triforine as active ingredients. The wettable powder thus obtained contains said active ingredients in a total amount of 50% and in a ratio of 3:7.

EXAMPLE 13

Wettable powder (77 WP)

In a laboratory blender 7% of compound I/17, 70% of Triforine 13% of Sipernat 50 as carrier, 2% of Netzer IS as wetting agent, 3% of Dispergiermittel 1494 and 5% of sulfite waste liquor powder as dispersing agents are mixed and finely ground in an Alpine 63 C type mill. The wettable composition thus obtained contains said two active ingredients in a total amount of 77% and in a ratio of 1:10.

EXAMPLE 14

Emulsifiable concentrate (35 EC)

25% of compound I/17, 5% of Carbendazim and 5% Triforine active ingredients are dissolved in the mixture of 32% of xylene and 25% dimethyl formamide and 6% of Emulsogen IP-400 and 2% of Emulsogen EL-400 are added to the solution and further the procedure of Example 1 is followed. The emulsifiable concentrate thus obtained contains said three active ingredients in a total amount of 35% and in a ratio of 5:1:1.

Following the above procedure but using any other compound of Table I together with Carbendazim and Triforine, similarly 35 EC compositions, containing three active ingredients, may be obtained.

EXAMPLE 15

Wettable powder (35 WP)

In a laboratory blender 25% compound I/17, 5% Carbendazim and 5% Triforin active ingredients, 35% of Sipernat 50 and 20% of siliceous earth as carriers, 2% of Netzer IS as wetting agent, 3% of Dispergiermittel 1494 and 5% of sulfite waste liquor powder as dispersing agents are admixed and finely ground in an Alpine 63C type mill. The wettable powder thus obtained contains said three active ingredients in a total amount of 35% and in a ratio of 5:1:1.

Following the above procedure but using any other compound of Table I together with Carbendazim and Triforine, similarly 35 WP compositions containing 35 WP may be obtained.

EXAMPLE 16

Emulsifiable concentrate (60 EC)

50% of compound I/17, 5% of Carbendazim and 5% Triforine are dissolved in the mixture of 16% of xylene and 16% of Isoforone (3,5,5-trimethyl-cyclohex-2-ene-one, GBP No. 2029415), 6% of Emulsogen IP-400 and 2% of Emulsogen EL-400 as emulsifying agents are added to the solution and further the procedure of Example 1 is followed. The emulsifiable concentrate thus obtained contains compound I/17, Carbendazim and Triforine, in a total amount of 60% and in a ratio of 10:1:1.

EXAMPLE 17

Wettable powder (84 WP)

In a laboratory blender 4% of compound I/17, 40% of Carbendazim, and 40% of Triforine as active ingredients, 8% of Sipernat 50 as carrier, 1.5% of Netzer IS as vetting agent, 2.5% of Dispergiermittel 1494 and 4% of sulfite waste liquor powder as dispersing agents are admixed and thereafter finely ground in an Alpine 63C type mill. The wettable powder thus obtained contains the compound I/17, Carbendazim and Triforine in a total amount of 84% and in a ratio of 1:10:10.

The fungicidal and acaricidal activity of the compositions prepared according to the above Examples 1–17 are shown by the following biological Examples.

EXAMPLE 18

Fungicidal activity against powdery mildew-conidia

The compositions of Examples 4, 5 and 6 containing compound I/17 and Triforine in ratios of 9:1, 7:1 and 3:1 were admixed with aqueous agar culture medium in a concentration of 2 mg active ingredient/liter, immediately before forming the plates. The two active ingredients were also tested separately, in a concentration of 0.2–10 mg active ingredient/liter, in form of a formulation prepared according to Examples 4 and 5.

Four different powdery mildew-conidia were taken from plants grown in green-house and tested on cellophane film placed onto agar plates. The test was carried out according to the method of Gy. Sz. Nagy, (Növényvédelem, XI. (9), /1975/, 397–400). The results obtained were calculated as inhibition % related to the untreated control.

The effect to be expected (synergistic effect) of the compositions was calculated according to Colby using the following equation:

$$\text{Efficiency \% } (E_i) = X + Y - \frac{XY}{100}$$

wherein

X is the effect of active ingredient A used at a ratio of p (kg/ha), calculated in the percentage of the control, Y is the effect of active ingredient B used at a ratio of q (kg/ha), calculated in the percentage of the control, $E_i$ is the synergistic effect using A+B at a ratio of p+q (kg/ha), calculated in the percentage of the control.

The calculated and found results are summarized in the following Table II.

TABLE II

| No. | Name of active ingredients | Amount mg/l | Ratio | Inhibition % of different powdery mildew species | | | | | |
|---|---|---|---|---|---|---|---|---|---|
| | | | | Sphaerotheca fuliginea | | | ERISIPHE betae | | |
| | | | | Calc. effect | Found effect % | Surplus effect | Calc. effect | Found effect % | Surplus effect |
| 1. | I/17 | 10 | | | 0 | | | 0 | |
| 2. | Triforine | 0.2 | | | 17 | | | 0 | |
| | | 0.25 | | | 33 | | | 67 | |
| | | 0.5 | | | 57 | | | 88 | |
| 3. | Triforine + I/17 | 0.2 1.8 | 1:9 | 17 | 70 | 53 | 0 | 99 | 99 |
| 4. | Triforine + I/17 | 0.25 1.75 | 1:7 | 33 | 80 | 47 | 67 | 99 | 32 |
| 5. | Triforine + I/17 | 0.5 1.5 | 1:3 | 57 | 100 | 43 | 88 | 100 | 12 |

| No. | Name of active ingredients | Amount mg/l | Ratio | Inhibition % of different powdery mildew species ERISIPHE | | | | | |
|---|---|---|---|---|---|---|---|---|---|
| | | | | heraclei | | | graminis | | |
| | | | | Calc. effect % | Found effect | Surplus effect % | Calc. effect | Found effect % | Surplus effect |
| 1. | I/17 | 10 | | | 0 | | | 10 | |
| 2. | Triforine | 0.2 | | 0 | | | 0 | | |
| | | 0.25 | | 0 | | | 0 | | |
| | | 0.5 | | 70 | | | 27 | | |
| 3. | Triforine + I/17 | 0.2 1.8 | 1:9 | 0 | 99 | 99 | 0 | 99 | 99 |
| 4. | Triforine + I/17 | 0.25 1.75 | 1:7 | 0 | 99 | 99 | 0 | 99 | 99 |
| 5. | Triforine + I/17 | 0.5 1.5 | 1:3 | 70 | 100 | 30 | 27 | 100 | 73 |

The data of the above Table II clearly show that the fungicides according to the invention possess a significant synergistic activity against all the four powdery mildew fungi.

EXAMPLE 19

Fungicidal activity against Colletotrichum atramentarium

The test described in Example 18 was repeated except that instead of powdery mildew the agar culture medium containing the compositions according to Examples 7-12 were infected with Colletotrichum atramentarium species. The calculated and found data are summarized in Table III.

TABLE III

| No. | Name of active ingredients | Amount mg/l | Ratio | Inhibition of development of colonies | | |
|---|---|---|---|---|---|---|
| | | | | Calc. effect % | Found effect % | Surplus effect % |
| 1. | I/17 | 25 | | | 30 | |
| | | 22.5 | | | 28 | |
| | | 20 | | | 27 | |
| | | 15 | | | 23 | |
| | | 12.5 | | | 21 | |
| | | 10 | | | 19 | |
| | | 7.5 | | | 12 | |
| 2. | Triforine | 2.5 | | | 4 | |
| | | 5.0 | | | 17 | |
| | | 10 | | | 26 | |
| | | 12.5 | | | 28 | |
| | | 15 | | | 29 | |
| | | 17.5 | | | 31 | |
| | | 25 | | | 35 | |

TABLE III-continued

| No. | Name of active ingredients | Amount mg/l | Ratio | Inhibition of development of colonies | | |
|---|---|---|---|---|---|---|
| | | | | Calc. effect % | Found effect % | Surplus effect % |
| 3. | I/17 + Triforine | 22.5 2.5 | 9:1 | 30.9 | 42 | 11.1 |
| 4. | I/17 + Triforine | 20 5 | 4:1 | 39.4 | 52 | 12.6 |
| 5. | I/17 + Triforine | 15 10 | 3:2 | 43.0 | 63 | 20.0 |
| 6. | I/17 + Triforine | 12.5 12.5 | 1:1 | 43.1 | 69 | 25.9 |
| 7. | I/17 + Triforine | 10 15 | 2:3 | 42.5 | 57 | 14.5 |
| 8. | I/17 + Triforine | 7.5 17.5 | 3:7 | 39.3 | 55 | 15.7 |

The data of the above Table III clearly show that the fungicides according to the invention possess a significant synergistic activity against Colletotrichum atramentarium. This activity shows a maximum value when the ratio of I/17 and Triforine is 1:1.

EXAMPLE 20

Fungicidal activity against powdery mildew of grape

The fungicidal activity of compositions comprising compounds of Table I in combination with Carbendazim or with Triforine against powdery mildew of grape was tested in small plots of grape culture. The tests were carried out in three repetitions using the compositions of Examples 1-3. The active ingredients were also tested separately in the form of 35 EC and 35 WP formulations prepared according to Examples 1-3.

The expected effect of the compositions containing two active ingredients was calculated by the Colby equation (see Example 18).

The calculated and found data are summarized in Table IV.

results were evaluated on Aug. 17 on the basis of the infection of 25-25 shoots.

TABLE IV

| Name of active ingredients | Amount g/ha | Activity against powdery mildew (Uncinula necator) | | | | |
|---|---|---|---|---|---|---|
| | | Infected leaf % | Infection related to the control, % | Calc. effect, % | Found effect, % | Surplus effect, % |
| I/17 | 350 | 59 | 86 | | 14 | |
| | 300 | 61 | 88 | | 12 | |
| I/3 | 350 | 57 | 83 | | 17 | |
| | 300 | 60 | 87 | | 13 | |
| I/56 | 350 | 54 | 78 | | 22 | |
| | 300 | 53 | 76.8 | | 23 | |
| Carbendazim | 350 | 29 | 42 | | 58 | |
| | 50 | 56 | 81 | | 19 | |
| Triforine | 350 | 8 | 12 | | 88 | |
| | 50 | 54 | 78 | | 22 | |
| I/17+ Carbendazim | 300+ 50 | 20 | 29 | 28.7 | 71 | 42.3 |
| I/17+ Triforine | 300+ 50 | 3 | 4 | 31.4 | 96 | 64.6 |
| I/3+ Carbendazim | 300+ 50 | 22 | 32 | 29.5 | 68 | 38.5 |
| I/3+ Triforine | 300+ 50 | 3 | 4 | 32.1 | 96 | 63.9 |
| I/56+ Carbendazim | 300+ 50 | 17 | 25 | 37.6 | 75 | 37.4 |
| I/56+ Triforine | 300+ 50 | 2 | 3 | 39.9 | 97 | 57.1 |
| Untreated Control | | 69 | 100 | | 0 | |

The data of the above Table clearly show that the compounds of Table I, the acaricidal activity of which is known first of all, possess a weak fungicidal activity (12-33%), the fungicidal activity of Carbendazim is somewhat higher (19-58%) and that of the Triforine, which is known as fungicidal compound, is 88% in a dose of 350 g/ha and 22% in a dose of 50 g/ha. However, admixing the compounds of Table I with Carbendazim or with Triforine in a ratio of 6:1 a significant synergistic effect (surplus effect) appears (37.4-64.6%) in case of treatments of powdery mildew of grape.

EXAMPLE 21

Fungicidal activity against powdery mildew of apple

Jonathan and Starking apple trees planted in a plot of 35 m² were treated at Jul. 27 against powdery mildew of apple (Podosphaera Lencotricha) using a spray in an amount of 700 l/ha, containing 350 g/ha of active ingredient, prepared from the 35 EC and 35 WP formulations according to Examples 14 and 15 respectively. The The active ingredients were also tested separately, in form of a formulation prepared according to Examples 14 and 15.

The expected effect of the compositions containing three active ingredients was calculated on the basis of the Colby equation in the following manner:

$$E_i = X + Y + Z - \frac{XY + XZ + YZ}{1000} + \frac{XYZ}{10000}$$

wherein

X is the effect of active ingredient A used at a ratio of p (kg/ha) and expressed in percentage of the control, Y is the effect of active ingredient B used at a ratio of q (kg/ha) and expressed in percentage of the control, Z is the effect of active ingredient C, used at a ratio of r (kg/ha) and expressed in percentage of the control, $E_i$ is the calculated effect of active ingredients A, B C used at a ratio of p+q+r (kg/ha), expressed in percentage of the control.

The calculated and found results are summarized in Table V.

TABLE V

| Name of active ingredients | Amount g/ha | Ratio | Activity against powdery mildew of apple | | | | |
|---|---|---|---|---|---|---|---|
| | | | Infected leaf % | Infection related to the control % | Fungicidal activity | | |
| | | | | | Calc. effect, % | Found effect, % | Surplus effect, % |
| I/17 | 350 | | 13.9 | 41 | | 59 | |
| | 250 | | 19.4 | 57 | | 43 | |
| I/3 | 350 | | 14.3 | 42 | | 58 | |
| | 250 | | 20.4 | 60 | | 40 | |
| I/56 | 350 | | 15.0 | 44 | | 56 | |
| | 250 | | 20.8 | 64 | | 36 | |
| Carbendazim | 350 | | 13.2 | 39 | | 61 | |
| | 50 | | 28.9 | 85 | | 15 | |
| Triforine | 350 | | 14.5 | 43 | | 57 | |
| | 50 | | 30.7 | 90 | | 10 | |
| I/17+ Carbendazim+ Triforine | 250+ 50+ 50 | 5:1:1 | 0 | 0 | 67.4 | 100 | 32.6 |
| I/3+ Carbendazim+ Triforine | 250+ 50+ 50 | 5:1:1 | 0.7 | 2 | 64.4 | 96 | 33.6 |

TABLE V-continued

| Name of active ingredients | Amount g/ha | Ratio | Activity against powdery mildew of apple | | | | |
|---|---|---|---|---|---|---|---|
| | | | Infection related | | Fungicidal activity | | |
| | | | Infected leaf % | to the control % | Calc. effect, % | Found effect, % | Surplus effect, % |
| I/56+ Carbendazim+ Triforine | 250+ 50+ 50 | 5:1:1 | 1.7 | 5 | 60.5 | 95 | 34.5 |
| Untreated Control | | | 34.06 | — | | | |

The data of Table V clearly show that the compositions containing compounds of Table I, or Carbendazim or Triforine as active ingredient possess about the same activity (56–61%) at a dose of 350 g, however the compositions containing the said three active ingredients in combination, in a ratio of 5:1:1, possess a significantly higher activity (95–100%) which means a surplus effect of 32–35% related to the calculated effect.

EXAMPLE 22

Acaricidal activity against red spider mite

Jonathan and Starking apple trees planted on a plot of 35 m² were treated on Jul. 27 against red spider mite (Panonychus ulmi), using a spray in an amount of 700 l/ha, containing 350 g/ha of active ingredient, prepared from the compositions of Examples 14 and 15. The number of mites was counted on Jul. 27 (before treatment), on Jul. 30 and on Aug. 3 under microscope using 100 leaves per treatment.

The active ingredients were also tested separately in formulations prepared according to Examples 14 and 15.

The efficacy of the compositions was calculated by the Henderson-Tilton formula (efficacy=percent mortality):

$$\% \text{ mortality} = 100 \times \left(1 - \frac{T_a \times C_b}{T_b \times C_a}\right)$$

wherein $T_a$ = the number of the living mites at the time of evaluation (after treatment)

$T_b$ = the number of the living mites at the beginning of the experiment (before treatment)

$C_a$ = the number of the living mites related to the untreated control at the time of evaluation $C_b$ = the number of the living mites related to the untreated control at the beginning of the experiment.

The result to be expected of the compositions containing three active ingredients was calculated by the Colby equation on the basis of their effect when using them individually (see Example 21). The calculated and found data are summarized in Table VI.

TABLE VI

| Name of active ingredients | Amount g/ha | Ratio | Activity against red spider mite | | | | | | | |
|---|---|---|---|---|---|---|---|---|---|---|
| | | | Number of mites/leaf | | | Efficacy % | | | | |
| | | | | | | on 3. day | | | on 7. day | | |
| | | | before the treatment | on 3. day after the treatment | on 7. day | Calc. effect % | Found effect % | Surplus effect % | Calc. effect % | Found effect % | Surplus effect % |
| Untreated Control | | | 23.8 | 26.8 | 24.3 | | | | | | |
| I/17 | 350 | | 14 | 2.4 | 2.1 | | 84.8 | | | 85.3 | |
| | 250 | | | 6.2 | 5.5 | | 60.5 | | | 61.2 | |
| I/3 | 350 | | 12.1 | 1.3 | 0.7 | | 90.5 | | | 94.3 | |
| | 250 | | | 4.0 | 3.4 | | 70.1 | | | 72.5 | |
| I/56 | 350 | | 16.7 | 2.0 | 0.9 | | 89.4 | | | 94.7 | |
| | 250 | | | 5.4 | 4.3 | | 71.3 | | | 74.6 | |
| Carbendazim | 350 | | 27.2 | 17.0 | 24.2 | | 44.5 | | | 12.9 | |
| | 50 | | | 19.5 | 24.7 | | 0 | | | 0 | |
| Triforine | 350 | | 14.1 | 19.7 | 17.8 | | 0 | | | 0 | |
| | 50 | | | 20.1 | 21.2 | | 0 | | | 0 | |
| I/17+ Carbendazim+ Triforine | 250 50 50 | 5:1:1 | 18.5 | 2.9 | 1.8 | 70.3 | 86.1 | 15.8 | 61.2 | 90.5 | 29.3 |
| I/3+ Carbendazim+ Triforine | 250 50 50 | 5:1:1 | 23.5 | 1.4 | 0.6 | 70.1 | 94.7 | 24.6 | 72.5 | 97.5 | 25.0 |
| I/56+ Carbendazim+ Triforine | 250 50 50 | 5:1:1 | 22.9 | 0.5 | 1.1 | 81.0 | 98.1 | 17.1 | 74.6 | 95.3 | 20.7 |

The data of the above Table clearly show that the compositions containing the compounds of Table I as active ingredient possess a significant acaricidal activity at the dose of 350 g/ha and 250 g/ha and 250 g/ha too. The composition containing Carbendazim shows acaricidal activity only at the dose of 350 g/ha and the composition containing Triforine as active ingredient is ineffective at both doses. The compositions comprising the combination of the three active ingredients in a ratio of 5:1:1 possess a significant acaricidal activity (86–98%) which is higher by 15–29% than the values to be expected (calculated values).

EXAMPLE 23

Acaricidal activity against grape mite

Oporto grape was used in the experiments. The plants were treated at the time of budding (Apr. 18) and at the stage of 2-5 leaflets (May 9). The compositions prepared according to Examples 1-3 were applied with spraying gun to the plants with 1000 l/ha of water, the dose of the active ingredient was 350 g/ha. The field evaluation was made before flowering of the grape (May 27) by counting the number of mites on a leaf surface of 10×5×5 mm.

The efficacy % of the composition was calculated by the Abbot-equation:

$$\text{Efficacy \%} = \frac{C - T}{C} \times 100$$

wherein
C=the number of the living mites in the control at the time of the evaluation,
T=the number of the living mites after the treatment The effect to be expected of the compositions containing two active ingredients was calculated by the Colby equation (see Example 18).

The calculated and found data are summarized in Table VII.

TABLE VII

| Name | Amount g/ha of active ingredients | Ratio | Activity against grape mite Number of mites on a leaf surface of 10 × 5 × 5 mm | Calc. effect % | Found effect % | Surplus effect % |
|---|---|---|---|---|---|---|
| I/17 | 350 | | 25 | | 88.5 | |
|  | 300 | | 41 | | 81.1 | |
| I/3 | 350 | | 16 | | 92.6 | |
|  | 300 | | 19 | | 91.2 | |
| I/56 | 350 | | 22 | | 89.9 | |
|  | 300 | | 28 | | 87.1 | |
| Carbendazim | 350 | | 203 | | 6.5 | |
|  | 50 | | 219 | | 0 | |
| Triforine | 350 | | 235 | | 0 | |
|  | 50 | | 228 | | 0 | |
| I/17 + Carbendazim | 300+ 50 | 6:1 | 15 | 81.1 | 93.1 | 12.0 |
| I/17 + Triforine | 300+ 50 | 6:1 | 23 | 81.1 | 89.4 | 8.3 |
| I/3 + Carbendazim | 300+ 50 | 6:1 | 2 | 91.2 | 99.1 | 7.9 |
| I/3 + Triforine | 300+ 50 | 6:1 | 7 | 91.2 | 96.8 | 5.6 |
| I/56 + Carbendazim | 300+ 50 | 6:1 | 9 | 87.1 | 95.9 | 8.8 |
| I/56 + Triforine | 300+ 50 | 6:1 | 4 | 87.1 | 98.2 | 11.1 |
| Untreated Control | | | 217 | | | |

The data of the above Table VII clearly show that the compositions containing the compound of Table I as active ingredient possess a significant acaricidal activity at doses of 350 g/ha and 300 g/ha too, however the compositions containing Carbendazim and Triforine are ineffective. The compositions comprising two active ingredients in a ratio of 6:1 show synergistic activity, the degree of which is 5.6–12%.

EXAMPLE 24

Emulsifiable concentrate 20 EC

14% of compound I/17, 3% of Triforine and 3% of copper-oxy-quinolate as active ingredients are dissolved in the mixture of 35% of xylene and 35% of dimethyl sulfoxide and to the solution thus obtained 6% of Atlox 4851 B (calcium alkyl-aryl sulfonate) and 4% of Altox 4857 B (fatty acid ethoxylate) as emulsifying agents are added and further the procedure of Example 1 is followed. The emulsifiable concentrate thus obtained contains compound I/17, Triforine and copper-oxy-quinolate in an amount of 20% and in a ratio of 14:3:3.

EXAMPLE 25

Emulsifiable concentrate 60 EC

20% of compound I/17, 15% of Triforine and 25% of copper-oxy-quinolate are dissolved in a solvent mixture comprising 14% of xylene and 20% of dimethyl-sulfoxide thereafter 4% of Atlox 4851 B and 2% of Atlox 4857 B are added to the solution and further the procedure of Example 1 is followed. The emulsifiable concentrate thus obtained contains the compound I/17, Triforine and copper-oxy-quinolate in an amount of 60% and in a ratio of 4:3:5.

EXAMPLE 26

Wettable powder (50 WP)

In a laboratory powder blender 35% of compound I/17 are sprayed onto 40% of Sipernat 50 S carrier thereafter 7.5% of Triforine and 7.5% of Thiabendazole (2-(thiazol-4-yl)-benzimidazole) as active ingredients, 2% of Netzer IS as wetting agent, 3% of Dispergiermittel 1494 and 5% of sulfite waste liquor powder as dispersing agents are added and further the procedure of Example 2 is followed. The wettable powder thus obtained comprises compound I/17, Triforine and Thiabendazole in an amount of 50% and in a ratio of 14:3:3.

EXAMPLE 27

Wettable powder (46 WP)

The procedure of Example 26 is followed except that 30% of compound I/17, 8% of Triforine and 8% of Thiabendazole, 44% of Sipernat 50 S, 1.5% of Netzer IS, 3.5% of Dispergiermittel 1494 and 5% of sulfite waste liquor powder are used. The wettable powder thus obtained comprises the compound I/17, Triforine and Thiabendazole in an amount of 46% and in a ratio of 3.75:1:1.

EXAMPLE 28

Emulsifiable concentrate (70 EC)

34.3% of compound I/17, 14.7% of Triforine and 21% of Metalaxyl (methyl-N-[2-methoxyacetyl]-N-[2,6-xylyl]-D,L-alaninate) active ingredients are dissolved under stirring in 24% of N-methyl pyrrolidone thereafter 5% of Emulsogen IP-400 and 1% of Emulsogen EL-400 are added as emulsifying agents and further the procedure of Example 1 is followed. The emulsifiable concentrate thus obtained comprises the compound I/17, Triforine and metalaxyl in an amount of 70% and in a ratio 4.9:2.1:3.

EXAMPLE 29

Emulsifiable concentrate (55 EC)

24% of compound I/17, 20% of Triforine and 10% of metalaxyl active ingredients are dissolved in 40% of N-methyl-pyrrolidone and 4% of Emulsogen IP-400 and 1% of Emulsogen EL-400 emulsifying agents are added to the solution and further the procedure of Example 1 is followed. The emulsifiable concentrate thus obtained comprises the compound I/17, Triforine and metalaxyl in an amount of 55% and in a ratio of 2.5:2:1.

EXAMPLE 30

Emulsifiable concentrate (50 EC)

24.5% compound I/17, 10.5% of Triforine and 15% of Benalaxyl (methyl-N-phenylacetyl-N-[2,6-xylyl]-D,L-alaninate) active ingredients are dissolved under stirring in the mixture of 22% of aromatol and 20% of dichloromethane and 6.5% of Emulsogen IP-400 and 1.5% of Emulsogen EL-400 are added to the solution and further the procedure of Example 1 is followed. The emulsifiable concentrate thus obtained comprises the compound I/17, Triforine and Benalaxyl in an amount of 50% and in a ratio of 4.9:2.1:3.

EXAMPLE 31

Emulsifiable concentrate (43 EC)

35% of compound I/17, 5% of Triforine and 3% of Ofurace (2-chloro-N-[2,6-dimethyl-phenyl]-N-tetrahydro-2-oxo-3-furanyl-acetamide) active ingredients are dissolved in the mixture of 25% of xylene and 25% of dimethyl formamide and thereafter 6% of Emulsogen IP-400 and 1% of Emulsogen-400 are added to the solution and further the procedure of Example 1 is followed. The emulsifiable concentrate thus obtained comprises the compound I/17, Triforine and Ofurace active ingredients in an amount of 43% and in a ratio of 11.7:1.7:1.

EXAMPLE 32

Emulsifiable concentrate (46 EC)

28% of compound I/17, 6% of Triforine and 14% of Ofurace active ingredients are dissolved in the mixture of 22% of aromatol and 22% of dimethyl formamide thereafter 7% of Emulsogen IP-400 and 1% of Emulsogen EL-400 emulsifying agents are added to the solution and further the procedure of Example 1 is followed. The emulsifiable concentrate thus obtained comprises the compound I/17, Triforine and Ofurace active ingredients in an amount of 48% and in a ratio of 14:3:7.

EXAMPLE 33

Emulsifiable concentrate

42% of compound I/17, 9% of Triforine and 9% of Ofurace active ingredients are dissolved in the mixture of 10% of xylene and 24% of dichloromethane thereafter 4.5% of Emulsogen IP-400 and 1.5% of Emulsogen EL-400 are added to the solution and further the procedure of Example 1 is followed. The emulsifiable concentrate thus obtained comprises the compound I/17, Triforine and Ofurace in an amount of 60% and in a ratio of 14:3:3.

EXAMPLE 34

Emulsifiable concentrate (65 EC)

24.5% of compound I/17, 10.5% of Triforine and 30% of Ofurace are dissolved in the mixture of 10% of xylene and 17% of dichloromethane thereafter 6.5% of Emulsogen IP-400 and 1.5% of Emulsogen EL-400 are added to the solution and further the procedure of Example 1 is followed. The emulsifiable concentrate thus obtained comprises the compound I/17, Triforine and Ofurace active ingredients in an amount of 65% and in a ratio of 4.9:2.1:6.

EXAMPLE 35

Emulsifiable concentrate (50 EC)

24.5% of compound I/17, 10.5% of Triforine and 15% of Oxadixyl (N-[2,6-dimethyl-phenyl]-2-methoxy-N-[2-oxo-3-oxazolidinyl]-acetamide) active ingredients are dissolved in the mixture of 22% of aromatol and 20% of dimethyl sulfoxide thereafter 1% of Tensiofix 7416 (octylphenol polyglycol ether) and 7% of Tensiofix 7438 (nonylphenol polyglycol ether) emulsifying agents are added to the solution and further the procedure of Example 1 is followed. The emulsifiable concentrate thus obtained comprises the compound I/17, Triforine and Oxadixyl active ingredients in an amount of 50% and in a ratio of 4.9:2.1:3.

EXAMPLE 36

Emulsifiable concentrate (50 EC)

24.5% of compound I/17, 10.5% of Triforine and 15% of Cyprofuram (N-[3-chlorophenyl]-N-[tetrahydro-2-oxo-3-furanyl]-cyclopropane carboxamide) active ingredients are dissolved in the mixture of 22% of aromatol and 22% of cyclohexanone thereafter 2% of Tensiofix 7416 and 6% of Tensiofix 7438 emulsifying agents are added and further the procedure of Example 1 is followed. The emulsifiable concentrate thus obtained comprises the compound I/17, Triforine and Cyprofuram active ingredients in an amount of 50% and in a ratio of 4.9:2.1:3.

EXAMPLE 37

Emulsifiable concentrate (65 EC)

24.5% of compound I/17, 10.5% of Triforine and 30% of Cyprofuram are dissolved in the mixture of 15% of aromatol and 12% of cyclohexanone thereafter 3% of Tensiofix 7416 and 5% of Tensiofix 7438 emulsifying agents are added to the solution and further the procedure of Example 1 is followed. The emulsifiable concentrate thus obtained comprises the compound I/17, Triforine and cyprofuram in an amount of 65% and in a ratio of 4.9:2.1:6.

EXAMPLE 38

Fungicidal activity against peronospora (Plasmopara halstedii), (curative treatment)

The sunflower plants infected with peronospora were treated with the aqueous solution of composition prepared according to Example 4 but containing only one active ingredient, i.e. compound I/17, or Triforine or copper-oxy-quinolate in an amount of 30-200 mg/l, and with the aqueous solution of composition prepared according to Example 24, containing the combination of three active ingredients in a concentration of 100-200 mg/l. The plants were kept for 24 hours in a humid chamber thereafter the activity of the compositions was evaluated on the basis of their effect produced on the inhibition of sporulation of Plasmopara halstedii. The treatment, the evaluation and calculation of the fungicidal activity were carried out according to the method of Oros and Virany (Annals of Applied Biology (Cambridge), 110, 1978, p 53-63). The active ingredients used in the tests, the amount and ratios thereof, the inhibition % of sporulation related to the untreated control and the percentage of the increase of efficacy of the composition containing three active ingredients are summarized in Table VIII.

The increase of efficacy, i.e. the synergistic effect was evaluated according to the following two methods:

(A) The efficacy of the combination was compared to the efficacy of the most effective component of the combination and the surplus effect was given in %, or (B) The effect to be expected was calculated by the Colby equation and compared to the effect found.

TABLE VIII

| No. | of the active ingredients | Amount mg/l | Inhibition of sporulation % | A % | B calc. effect % | Surplus effect % |
|---|---|---|---|---|---|---|
| 1. | I/17 | 200 | 26 | | | |
| | I/17 | 140 | 14 | | | |
| | I/17 | 100 | 7 | | | |
| | I/17 | 70 | 3 | | | |
| | I/17 | 50 | 0 | | | |
| 2. | Triforine | 200[x] | 51 | | | |
| | Triforine | 100 | 22 | | | |
| | Triforine | 50 | 5 | | | |
| | Triforine | 30 | 0 | | | |
| 3. | Copper-oxy-quinolate | 200 | 40 | | | |
| | Copper-oxy-quinolate | 100 | 6 | | | |
| | Copper-oxy-quinolate | 50 | 0 | | | |
| 4. | 1 + 2 + 3 (14:3:3) | 200 | 72 | +21 | 14 | 58 |
| | 1 + 2 + 3 (14:3:3) | 100 | 48 | +26 | 3 | 45 |

[x]it caused phytotoxic symptoms on sunflower plants

The data of the above Table show clearly that the composition according to Example 24 containing three active ingredients possesses a significant synergistic activity against peronospora, compared to Triforine—being the most effective among the compositions containing one active ingredient—as well as to the expected effect calculated by the Colby equation.

EXAMPLE 39

Fungicidal activity against peronospora (leaf treatment)

The test described in Example 38 was repeated, except that the treatments were carried out by using the aqueous suspensions of compositions prepared according to Example 5 but containing only one active ingredient, i.e. compound I/17, Triforine or Thiabendazole in a concentration of 30-200 mg/l and the aqueous suspensions of the preparation containing three active ingredients and prepared according to Examples 26 and 27.

The results obtained are summarized in Table IX.

TABLE IX

| No. | Name of the active ingredients | Amount mg/l | Inhibition of sporulation % | A % | B calc. effect % | Surplus effect % |
|---|---|---|---|---|---|---|
| 1. | I/17 | 200 | 26 | | | |
| | I/17 | 140 | 14 | | | |
| | I/17 | 100 | 7 | | | |
| | I/17 | 70 | 3 | | | |
| | I/17 | 50 | 0 | | | |
| 2. | Triforine | 200[x] | 51 | | | |
| | Triforine | 100 | 22 | | | |
| | Triforine | 50 | 5 | | | |
| | Triforine | 30 | 0 | | | |
| 3. | Thiabendazole | 200 | 10 | | | |
| | Thiabendazole | 100 | 3 | | | |
| | Thiabendazole | 30 | 0 | | | |
| 4. | 1 + 2 + 3(14:3:3) | 200 | 61 | +10 | 14 | 47 |
| | 1 + 2 + 3(14:3:3) | 100 | 24 | +2 | 3 | 21 |
| | 1 + 2 + 3(3.75:1:1) | 100 | 20 | −2 | 0 | 20 |

[x]it caused phytotoxic symptoms on sunflower plants

The data of the above Table clearly show that the compositions containing one active ingredient possess a weak activity against peronospora even at a concentration of 200 mg/l, except Triforine which shows a medium fungicidal activity at this concentration, however it is harmful to the sunflower. Among the compositions containing three active ingredients the composition according to Example 26 is effective at the dose of 200 mg/l, however it does not cause phytotoxic symptoms.

EXAMPLE 40

Fungicidal activity against peronospora (eradicative effect)

10 mm pieces were cut out from hypocotyl of sunflower plants and floated for 1 hour in aqueous solutions of compositions prepared according to Example 7 but comprising only one active ingredient, i.e. compound I/17, Triforine or Metalaxyl and of composition prepared according to Example 28 and containing three active ingredients, containing the active ingredients in a concentration of 5.3–100 mg/l. Thereafter the segments were incubated in humid chamber for 24 hours then evaluated under microscope whether the thallus of the fungus was destroyed or not. The fungicidal activity was expressed as inhibition % related to the untreated control.

The synergistic effect of the compositions comprising three active ingredients was calculated according to both methods described in Example 38. The results obtained are summarized in Table X.

TABLE X

| | | | | Increase of efficacy, % | | |
|---|---|---|---|---|---|---|
| No. | Name of the active ingredients | Amount mg/l | Inhibition of sporulation % | A % | B calc. effect % | Surplus effect % |
| 1. | I/17 | 100 | 30 | | | |
| | I/17 | 50 | 19 | | | |
| | I/17 | 25 | 11 | | | |
| | I/17 | 12.3 | 6 | | | |
| 2. | Triforine | 100 | 37 | | | |
| | Triforine | 50 | 18 | | | |
| | Triforine | 25 | 7 | | | |
| | Triforine | 21 | 5.5 | | | |
| | Triforine | 10.5 | 1.5 | | | |
| | Triforine | 5.3 | 0 | | | |
| 3. | Metalaxyl | 100 | 50 | | | |
| | Metalaxyl | 50 | 43 | | | |
| | Metalaxyl | 30 | 38 | | | |
| | Metalaxyl | 25 | 36 | | | |
| | Metalaxyl | 15 | 31 | | | |
| | Metalaxyl | 7.5 | 25 | | | |
| 4. | 1 + 2 + 3(4.9:2.1:3) | 100 | 74 | +24 | 61.9 | 12.1 |
| | | 50 | 62 | +20 | 43.2 | 18.8 |
| | | 25 | 48 | +18 | 30.9 | 17.1 |

The data of the above Table clearly show that the compositions containing only compound I/17 or Triforine as active ingredient are very weak fungicides even in a dose of 100 mg/l. The composition containing metalaxyl as active ingredient is a medium fungicide. However the composition prepared according to Example 28 and containing three active ingredients shows a good fungicidal activity even at a concentration of 50 mg/l and possesses a better fungicidal activity, at a quarter of the above dose (25 mg/l), than the compositions containing only compound I/17 or Triforine at a concentration of 100 mg/l. The synergistic effect exists at all three concentration values whether it is compared to the composition containing metalaxyl or to the result to be expected calculated by the Colby equation.

EXAMPLE 41

Fungicidal activity against peronospora (leaf treatment)

The test-series of Example 38 was repeated except that compositions prepared according to Example 7 but containing only one active ingredient, i.e. compound I/17 or Triforine or Benalaxyl as well as a composition containing three active ingredients, prepared according to Example 30 were used in form of aqueous solutions containing 25–100 mg/l active ingredient. The results obtained are summarized in Table XI.

TABLE XI

| | | | | Increase of efficacy, % | | |
|---|---|---|---|---|---|---|
| No. | Name of the active ingredients | Amount mg/l | Inhibition of sporulation % | A % | B calc. effect % | Surplus effect % |
| 1. | I/17 | 100 | 7 | | | |
| | I/17 | 50 | 0 | | | |
| 2. | Triforine | 100 | 22 | | | |
| | Triforine | 25 | 0 | | | |
| 3. | Benalaxyl | 100 | 13 | | | |
| | Benalaxyl | 25 | 0 | | | |
| 4. | 1 + 2 + 3(4.9:2.1:3) | 100 | 63 | +41 | 0 | 63 |

The data of the above Table clearly show that the compositions containing only one active ingredient possess a very poor fungicidal activity against peronospora, however the composiion containing three active ingredients show a significant inhibition of sporulation. The synergistic effect calculated according to both above methods is significant.

EXAMPLE 42

Fungicidal activity against peronospora (eradicative effect)

The tests of Example 40 were repeated but the treatments were carried out with the composition of Example 41. The results obtained are summarized in Table XII.

TABLE XII

| No. | Name of the active ingredients | Amount mg/l | Inhibition % | Increase of efficacy, % | | |
|---|---|---|---|---|---|---|
| | | | | A % | B calc. effect % | Surplus effect % |
| 1. | I/17 | 100 | 30 | | | |
| | I/17 | 49 | 19 | | | |
| 2. | Triforine | 100 | 37 | | | |
| | Triforine | 21 | 5.5 | | | |
| 3. | Benalaxyl | 100 | 42 | | | |
| | Benalaxyl | 30 | 21 | | | |
| 4. | 1 + 2 + 3 (4.9:2.1:3) | 100 | 57 | +15 | 45 | 12 |

The data of the above Table clearly show that the composition containing three active ingredients and prepared according to Example 30 is more effective than the best composition containing only one active ingredient. The synergistic effect can be shown by both above mentioned methods.

EXAMPLE 43

Fungicidal activity against peronospora (leaf treatment)

The test-series of Example 38 was repeated except that compositions prepared according to Example 7 but comprising only one active ingredient, i.e. compound I/17 or Triforine or Ofurace and compositions according to Example 31, 32 and 33, comprising three active ingredients were used in form of aqueous solutions, containing 20–200 mg/l active ingredient. The results obtained are summarized in Table XIII.

TABLE XIII

| No. | Name of the active ingredients | Amount mg/l | Inhibition of sporulation % | Increase of efficacy, % | | |
|---|---|---|---|---|---|---|
| | | | | A % | B calc. % | Surplus effect % |
| 1. | I/17 | 200 | 26 | | | |
| | I/17 | 125 | 12 | | | |
| | I/17 | 100 | 7 | | | |
| | I/17 | 81.4 | 4.1 | | | |
| | I/17 | 73 | 3.6 | | | |
| | I/17 | 70 | 3 | | | |
| | I/17 | 50 | 0 | | | |
| 2. | Triforine | 200* | 51 | | | |
| | Triforine | 125 | 31 | | | |
| | Triforine | 100 | 22 | | | |
| | Triforine | 50 | 5 | | | |
| | Triforine | 20 | 0 | | | |
| 3. | Ofurace | 200 | 12 | | | |
| | Ofurace | 125 | 9 | | | |
| | Ofurace | 100 | 8 | | | |
| | Ofurace | 50 | 0 | | | |
| 4. | 1 + 2 + 3 (11.7:1.7:1) | 100 | 27 | +5 | 4.1 | 22.9 |
| | 1 + 2 + 3 (14:3:7) | 125 | 79 | +42 | 3.6 | 75.4 |
| | 1 + 2 + 3 (14:3:3) | 100 | 70 | +48 | 3.0 | 67.0 |

*it caused phytotoxic symptoms on sunflower plants

The data of the above Table show that the compositions according to Examples 31, 32 and 33 possess synergistic fungicidal activity. This effect is especially strong in case of compositions of Examples 30 and 31 which are more effective in a concentration of 100–125 mg/l than the composition containing one active ingredient in a concentration of 200 mg/l.

EXAMPLE 44

Fungicidal activity against peronospora (eradicative effect)

The tests of Example 40 were repeated except that compositions prepared according to Example 7 and comprising only one active ingredient, i.e. compound I/17 or Triforine Ofurace and composition prepared according to Example 34 and comprising three active ingredients were used in the form of aqueous solutions containing 20–125 mg/l active ingredient. The results obtained are summarized in Table XIV.

TABLE XIV

| No. | Name of the active ingredients | Amount mg/l | Inhibition % | Increase of efficacy, % | | |
|---|---|---|---|---|---|---|
| | | | | A % | B calc. effect % | Surplus effect % |
| 1. | I/17 | 125 | 32 | | | |
| | I/17 | 50 | 19 | | | |
| | I/17 | 47 | 18 | | | |
| 2. | Triforine | 125 | 43 | | | |
| | Triforine | 25 | 7 | | | |
| | Triforine | 20 | 5 | | | |
| 3. | Ofurace | 125 | 80 | | | |
| | Ofurace | 60 | 58 | | | |
| | Ofurace | 58 | 56 | | | |
| 4. | 1 + 2 + 3 (4.9:2.1:6) | 125 | 89 | +9 | 78.1 | 10.9 |

The data of the above Table clearly show that the composition according to Example 34, containing three active ingredients possesses a better fungicidal activity than the known and widely used composition containing Ofurace as active ingredient.

EXAMPLE 45

Fungicidal activity against peronospora (eradicative effect)

The test-series of Example 40 was repeated but composition prepared according to Example 7 and containing only one active ingredient, i.e. compound I/17 or Triforine or Oxadixyl and composition prepared according to Example 35 and containing three active ingredients were used in form of aqueous solutions containing 21–100 mg/l active ingredient. The results obtained are summarized in Table XV.

TABLE XV

| No. | Name of the active ingredients | Amount mg/l | Inhibition % | Increase of efficacy, % | | |
|---|---|---|---|---|---|---|
| | | | | A % | B calc. effect % | Surplus effect % |
| 1. | I/17 | 100 | 30 | | | |
| | I/17 | 49 | 19 | | | |
| 2. | Triforine | 100 | 37 | | | |
| | Triforine | 21 | 5.5 | | | |
| 3. | Oxadixyl | 100 | 31 | | | |
| | Oxadixyl | 30 | 0 | | | |
| 4. | 1 + 2 + 3 (4.9:2.1:3) | 100 | 96 | +59 | 24.4 | 71.6 |

The data of the above Table clearly show that the compositions comprising only one active ingredient possess a poor fungicidal activity, however the composition according to Example 35 containing three active ingredients has nearly a 100% efficacy against said fungal diseases due to the significant synergistic effect.

EXAMPLE 46

Fungicidal activity against peronospora (eradicative effect)

The tests of Example 40 were repeated but compositions prepared according to Example 7 and comprising only one active ingredients, i.e. compound I/17 or Triforine or Cyprofuram and composition prepared according to Example 36 and comprising three active ingredients were used in form of aqueous solutions containing 21–125 mg/l active ingredient. The results obtained are summarized in Table XVI.

TABLE XVI

| No. | Name of the active ingredients | Amount mg/l | Inhibition % | A % | B calc. effect % | Surplus effect % |
|---|---|---|---|---|---|---|
| 1. | I/17 | 125 | 32 | | | |
| | I/17 | 100 | 30 | | | |
| | I/17 | 49 | 19 | | | |
| | I/17 | 47 | 18 | | | |
| 2. | Triforine | 125 | 43 | | | |
| | Triforine | 100 | 37 | | | |
| | Triforine | 25 | 7 | | | |
| | Triforine | 21 | 5.5 | | | |
| 3. | Cyprofuram | 125 | 84 | | | |
| | Cyprofuram | 100 | 80 | | | |
| | Cyprofuram | 57.7 | 51 | | | |
| | Cyprofuram | 30 | 21 | | | |
| 4. | 1 + 2 + 3 (4.9:2.1:3) | 100 | 61 | −19 | 45.1 | 15.9 |
| | 1 + 2 + 3 (4.9:2.1:6) | 125 | 88 | +4 | 62.3 | 25.7 |

The data of the above Table show that the synergistic effect appears if the compound I/17, Triforine and Cyprofuram active ingredients are admixed in a ratio of 4.9:2.1:6.

EXAMPLE 47

Fungicidal activity against powdery mildew of apple and cucumber

Apple leaves infected with Podosphera leucotricha and cucumber leaves infected with Sphaerotheca fuliginea were separated and bathed for 60 minutes in the 15–1000 mg/l aqueous solution of composition prepared according to Example 7 and comprising one, two or three active ingredients, thereafter they were placed onto polystyrene balls floated on water. The treated leaves were thereafter kept in diffuse light for two days and the fungicidal activity was evaluated under microscope. The treatment was considered to be successful when the formation of conidia was totally inhibited (100%) in all the treated 50 colonies. The results obtained are summarized in Table XVII and are characterized by concentration interval, the lower limit of which represents the value at which at least one conidium has formed and the upper limit corresponds to the concentration value at which total inhibition takes place.

TABLE XVII

| No. | Name of active ingredients | Ratio | Inhibition concentration for powdery mildew mg/l Apple | Cucumber |
|---|---|---|---|---|
| 1. | I/17 | | 500–1000 | 250–500 |
| 2. | Triforine | | 125–250 | 125–250 |
| 3. | Thiabendazole | | 250–500 | 250–500 |
| 4. | I/17 + Triforine | 7:3 | 62.5–125 | 62.5–125 |
| | | 7:5 | 62.5–125 | 62.5–125 |
| | | 1:1 | 125–250 | 125–250 |
| | | 3:7 | 125–250 | 125–250 |
| 5. | I/17 + Thiabendazole | 7:2 | 62–125 | 62.5–125 |
| | I/17 + Thiabendazole | 1:1 | 125–250 | 125–250 |
| | | 2:7 | 125–250 | 250–500 |
| 6. | Triforine + Thiabendazole | 2:1 | 125–250 | 125–250 |
| | | 1:1 | 125–250 | 125–250 |
| | | 1:2 | 125–250 | 250–500 |
| 7. | 1 + 2 + 3 | 7:3:2 | 31.25–62.5 | 16–62.5 |
| | | 7:2:1 | 62.5–125 | 31.25–125 |
| | | 7:1:2 | 125–500 | 125–250 |
| 8. | 1 + 2 + 3 | 3:1:1 | 125–250 | 125–500 |
| | | 5:1:4 | 125–250 | 125–250 |

The data of the above Table clearly show that the compositions comprising two or three active ingredients are fungicidally active, i.e. produce a 100% inhibition at a much more lower dose than the compositions containing only one active ingredient, i.e. compound I/17 or Thiabendazole. In five cases the combinations (I/17+Triforine=7:3 and 7:5, I/17 3+Thiabendazole=7:2, 1+2+3=7:3:2 and 7:2:1) possess better activity than the composition containing only Triforine.

EXAMPLE 48

Fungicidal activity against Cytospora cincta

Picnoconidium suspension of Cytospora cincta was spred uniformly on the surface of potato-dextrose culture medium. 25 μg of each active ingredient listed in Table XVIII were absorbed by strips of filter paper of 50×40 mm and two of strips were placed onto the surface of culture mediums infected rectangularly. The Petri dishes were incubated for 96 hours at 25° C. thereafter the results obtained were evaluated on the basis of the shape of the formed inhibition zones. The cases where interaction took place between the active ingredients are marked with '+' in Table XVIII.

TABLE XVIII

| Name of the active ingredients | I/17 | Components of the combinations Triforine | I/17 + Triforine |
|---|---|---|---|
| I/17 | | + | |
| Benalaxyl | | | + |
| Cyprofuram | | | + |
| F-849 | + | | + |
| Folpet | + | + | + |
| Iprodione | + | | + |
| Captafole | | | + |
| Mankozeb | + | | + |
| Nystatine | | | + |
| Ofurace | | | + |
| Quintozene | + | | + |
| S-39475 | | | + |

EXAMPLE 49

Acaricidal activity against spider mite on soya plants

Recently spider mites have damaged the soya plants too beside the apple cultures. As the importance and so the sowing area of soya is increasing, the effect of the compositions according to the invention was tested on soya too.

In 50 m² parcels soya plants were planted on April 24. The experiment started on July 22 at 10 different places by counting the number of mites on 2×3 top-leaves taken from 5 plants. The treatment was carried out on July 25 by spraying the plants with the 0.75–2.33 kg/ha aqueous solutions of composition prepared according to Example 7 and comprising only one active ingredient, i.e. compound I/17, or Triforine or copper-oxy-quinolate or Metalaxyl and of the composition prepared according to Examples 25 and 29 containing three active ingredients, 3 and 7 days after the treatments the number of the living mites was counted under microscope on 100 leaves per treatment. The efficiency of the compositions was calculated by the Henderson-Tilton equation as described in Example 22. The data calculated and found are summarized in Table XIX.

TABLE XIX

| No. | Name of active ingredients | Amount | Ratio | Number of spider mites | | Efficiency % | |
| | | | | Before the treatment | 3 days / 7 days after the treatment | After 3 days | After 7 days |
|---|---|---|---|---|---|---|---|
| 1. | I/17 | 0.9 | | 366 | 69.6   80.3 | 84.26 | 80.5 |
| 2. | | 1.9 | | 366 | 50.8   56.4 | 88.5 | 86.3 |
| 3. | Triforine | 0.32 | | 366 | 440    413 | 0 | 0 |
| 4. | | 0.48 | | 366 | 438    410 | 0 | 0 |
| 5. | Copper-oxy-quinolate | 2.33 | | 366 | 375    346.8 | 15.2 | 16.0 |
| 6. | Metalaxyl | 0.75 | | 366 | 361    363 | 18.3 | 12.0 |
| 7. | I/17 + Triforine + Copper-oxy-quinolate | 0.43 0.32 0.54 | 4:3:5 | 366 | 58.3   77.1 | 86.8 | 81.3 |
| 8. | I/17 + Triforine + Copper-oxy-quinolate | 0.64 0.48 0.80 | 4:3:5 | 366 | 35.8   26.4 | 91.9 | 93.6 |
| 9. | I/17 + Triforine + Metalaxyl | 0.405 0.324 0.162 | 2.5:2:1 | 366 | 68.5   80.0 | 84.5 | 80.6 |
| 10. | I/17 + Triforine + Metalaxyl | 0.60 0.48 0.24 | 2.5:2:1 | 366 | 17.7   17.3 | 96.0 | 95.8 |
| 11. | Untreated control | | | 366 | 442    412 | — | — |

The above data show that the compositions containing only Triforine or copper-oxy-quinolate or Metalaxyl are ineffective or have only a very poor activity against spider mites, however the compositions comprising these active ingredients in combination with compound I/17 possess a very good acaricidal activity. The lower dose of compositions containing three active ingredients and comprising compound I/17 in an amount of 0.405–0.43 kg/ha are more effective than the compositions containing only compound I/17 in an amount of 0.9 kg/ha. Moreover the higher doses of said compositions, comprising the compound I/17 in an amount of 0.6–0.64 kg/ha are significantly better than the compositions comprising compound I/17 in a three-times higher amount (1.9 kg/ha).

The foregoing Example 18–23 and 38–49 prove that the compositions according to the invention comprising two or three active ingredients possess a synergistic fungicidal and acaricidal activity and may be used by a simple and economical way for combating simultaneously mites and fungi.

What we claim is:

1. A synergistic fungicidal and acaricidal composition which comprises as active ingredients in a synergistic weight ratio of 5:1:1
   (a) a compound selected from the group consisting of:

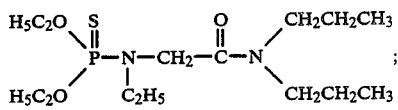

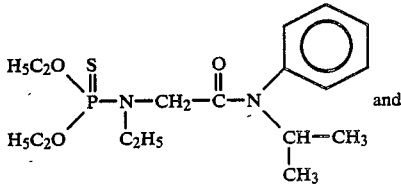

and

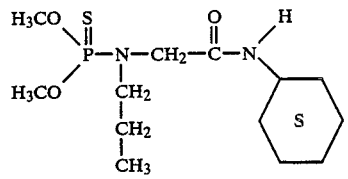

(b) Triforine; and
   (c) Carbendazim.

2. The synergistic fungicidal or acaricidal composition defined in claim 1 wherein the compound of (a) is:

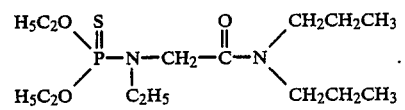

3. A method of treating a crop against a fungal or an acaricidal infection which comprises the step of applying to the crop a synergistic effective amount of the fungicidal or acaricidal composition defined in claim 1.